United States Patent
Ries et al.

(10) Patent No.: US 10,040,021 B2
(45) Date of Patent: Aug. 7, 2018

(54) FRAMES FOR IMPLANTABLE MEDICAL DEVICES AND METHODS

(71) Applicant: MEDTRONIC, INC., Minneapolis, MN (US)

(72) Inventors: Andrew J. Ries, Lino Lakes, MN (US); SuPing Lyu, Maple Grove, MN (US); Catherine M. Asgian, Coon Rapids, MN (US); David Engmark, Bethel, MN (US); Ananta Pandey, Mounds View, MN (US); Todd Schaefer, Mounds View, MN (US); Erik Scott, Maple Grove, MN (US); Joachim Hossick-Schott, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 649 days.

(21) Appl. No.: 14/593,588

(22) Filed: Jan. 9, 2015

(65) Prior Publication Data
US 2015/0196867 A1    Jul. 16, 2015

Related U.S. Application Data

(60) Provisional application No. 61/926,042, filed on Jan. 10, 2014.

(51) Int. Cl.
*A61N 1/375* (2006.01)
*B01D 53/04* (2006.01)
(Continued)

(52) U.S. Cl.
CPC ......... *B01D 53/0407* (2013.01); *A61N 1/375* (2013.01); *H01M 2/1022* (2013.01);
(Continued)

(58) Field of Classification Search
CPC ....................................... A61N 1/375–1/3758
See application file for complete search history.

(56) References Cited

U.S. PATENT DOCUMENTS

| | | | |
|---|---|---|---|
| 5,456,698 A | 10/1995 | Byland et al. | |
| 5,873,899 A | * 2/1999 | Stutz, Jr. | ........ A61N 1/375 607/36 |

(Continued)

FOREIGN PATENT DOCUMENTS

| | | |
|---|---|---|
| EP | 1112175 A1 | 12/1999 |
| EP | 2082781 A2 | 7/2009 |

OTHER PUBLICATIONS

International Search Report and Written Opinion dated Apr. 21, 2015, for International Application No. PCT/US2015/010829; 9 pages.

(Continued)

*Primary Examiner* — George Evanisko

(57) ABSTRACT

Frame structures, assemblies and methods for use in implantable medical devices. The frames may include one or more first polymeric portions and one or more second polymeric portions coupled to the one or more first polymeric portions. The one or more first polymeric portions may have a higher durometer than the one or more second polymeric portions. The one or more second polymeric portions may provide an interference fit between the one or more second polymeric portions and the housing and/or between the one or more second polymeric portions and one or more components disposed in the housing.

27 Claims, 11 Drawing Sheets

(51) Int. Cl.
*H01M 2/10* (2006.01)
*H01M 10/42* (2006.01)

(52) U.S. Cl.
CPC ....... *H01M 10/4264* (2013.01); *A61N 1/3758* (2013.01); *B01D 2253/102* (2013.01); *B01D 2253/1122* (2013.01); *B01D 2253/202* (2013.01); *B01D 2257/108* (2013.01); *B01D 2257/80* (2013.01); *H01M 2220/30* (2013.01); *Y10T 29/49108* (2015.01)

(56) References Cited

U.S. PATENT DOCUMENTS

| | | |
|---|---|---|
| 6,493,960 B2 | 12/2002 | Taylor |
| 6,685,452 B2 | 2/2004 | Christiansen |
| 6,799,072 B2 | 9/2004 | Ries |
| 7,798,476 B2 | 9/2010 | Utschig |
| 2012/0065500 A1 | 3/2012 | Rogers |
| 2012/0065503 A1 | 3/2012 | Rogers |

OTHER PUBLICATIONS

Schuessler et al., "The Effects of Hydrogen on Device Reliability," *Hybrid Circuit Technology*, 8, 1991, pp. 19-26.
Kullberg et al., "Getters for Microelectronic Packages," *Advanced Packaging 13*, (12), 2004, pp. 30-33.
Cookson Semiconductor Packaging Materials, STAYDRY™, Patented Technology, H2-3000-Hydrogen and Moisture Getter, *Technical Bulletin*, Jan. 2006, 2 pages.

\* cited by examiner

FRAMES FOR IMPLANTABLE MEDICAL DEVICES AND METHODS

RELATED APPLICATION

This application claims the benefit under 35 U.S.C. Section 119 of U.S. Provisional Patent Application No. 61/926,042 filed on Jan. 10, 2014 and titled FRAMES FOR IMPLANTABLE MEDICAL DEVICES, AND METHODS, the entire disclosure of which is hereby incorporated by reference.

BACKGROUND

A wide variety of implantable medical devices (IMDs) are known in the art. In general, IMD sizes continue to be reduced, including a move towards smaller volume housings and smaller components within the IMD, while maintaining structural integrity and functionality of the devices.

Components that provide structural integrity to the IMD include frames. Conventional IMDs may include a frame made of rigid thermoplastic and other internal components generally being affixed to the housing with epoxy to lock the components into place. These IMD assemblies are subject to loose rattling of components in the device.

Of particular interest are IMDs that include electronics such as processors, capacitors, wiring, batteries, etc., which are subject to potential corrosion as a result of moisture within the IMD. Examples of such IMDs that include electronics include sensing or monitoring devices, signal generators (such as cardiac pacemakers or defibrillators), neurostimulators (such as spinal cord stimulators, brain or deep brain stimulators, peripheral nerve stimulators, vagal nerve stimulators, occipital nerve stimulators, subcutaneous stimulators, etc.), gastric stimulators, infusion devices, hearing implants, cochlear implants, vision implants, and the like.

To reduce any presence of moisture within the IMD after it has been hermetically sealed during the manufacturing process, desiccant materials have been included in such IMDs to absorb at least some of the moisture present, including moisture released from plastic components in the IMD after the IMD is hermetically sealed. Traditionally, a thermoset polymer, such as silicone, has been used to carry the desiccant material and occupy a free-space within the IMD.

There is still a need for mechanisms that provide structural rigidity in increasingly smaller devices, limiting moisture uptake of a desiccant during manufacturing, while providing sufficient moisture uptake after sealing an IMD.

SUMMARY

The problems with providing structural rigidity in increasingly smaller devices, and the problems with limiting the moisture uptake of a desiccant during manufacturing, while still providing sufficient moisture uptake after sealing an IMD, may be addressed by the frame, assemblies, and methods described herein. For example, in certain embodiments, an exemplary frame and IMD assembly may be compact while providing structural rigidity and the ability to absorb manufacturing tolerance variations between the components. Also, in certain embodiments, an exemplary frame and IMD assembly may limit the amount of moisture absorbed during the manufacturing process (e.g., prior to being hermetically sealed) while still providing adequate moisture absorption after sealing.

One exemplary IMD may include a housing configured to be sealed (e.g., hermetically sealed or otherwise), and a frame that provides structural rigidity and limits relative movement of the components within the IMD assembly. The exemplary IMD may include electronic components, such as a processor, circuit board, battery, or capacitors.

One exemplary frame for use within an IMD may include polymeric portions of various durometers coupled to one another. An exemplary frame may include one or more first polymeric portions, and one or more second polymeric portions. In certain embodiments, at least one of (preferably, all of) the one or more first polymeric portions have a higher durometer than at least one of (preferably, all of) the one or more second polymeric portions. Although this may be preferred in certain situations, in certain other embodiments, at least one of (preferably, all of) the one or more first polymeric portions and at least one of (preferably, all of) the one or more second polymeric portions are of the same material.

In one exemplary embodiment, the one or more first polymeric portions are formed of a rigid thermoplastic polymer and the one or more second polymeric portions are formed of an elastomeric thermoplastic or thermoset polymer. However, either of the first polymeric portions or the second polymeric portions may be formed of any suitable polymer including thermoplastics or thermosets. In some embodiments either or both of the first or the second polymeric portions may include a desiccant material for absorbing moisture.

In one embodiment, the present disclosure provides an IMD that includes a housing defining an interior space; one or more components disposed in the interior space of the housing; and a frame disposed in the interior space of the housing. Preferably, the frame includes: one or more first polymeric portions and one or more second polymeric portions coupled to the one or more first polymeric portions, wherein at least one of the one or more first polymeric portions has a higher durometer than at least one of the one or more second polymeric portions. Also, the one or more second polymeric portions provides an interference fit between the one or more second polymeric portions and at least one of the housing and the one or more components disposed in the interior space of the housing.

In another embodiment, the present disclosure provides a method of manufacturing an implantable medical device. The method includes: providing a housing defining an interior space; providing one or more components; providing one or more first polymeric portions; coupling one or more second polymeric portions to the one or more first polymeric portions to form a frame; inserting the one or more components and the frame into the interior space of the housing; and closing the housing, providing an interference fit between the one or more second polymeric portions and at least one of the housing and the one or more components. At least one of the one or more first polymeric portions has a higher durometer than at least one of the one or more second polymeric portions. Preferably, all of the first polymeric portions have a higher durometer than all of the second polymeric portions. In certain embodiments, the first polymeric portion is a single portion.

As used herein, an elastomeric polymer is a polymer with viscoelasticity (i.e., "elasticity"). The term is sometimes used interchangeably with "elastic polymer." An elastomeric polymer is typically a thermoset polymer, but may also be a thermoplastic polymer.

A thermoset polymer (i.e., thermosetting polymer) is a polymer material that irreversibly cures. Thermosets often do not melt, but break down and do not reform upon cooling. In contrast, a thermoplastic polymer is a polymer that becomes pliable or moldable above a specific temperature, and returns to a solid state upon cooling. Thermoplastic polymers may provide a manufacturing advantage of being compatible with conventional injection molding machines.

The term "coupled" in the context of the first and second polymeric portions being coupled together means that they are integrally joined together either through chemical adhesion (with or without an adhesive), physical compression, physical entanglement, or other mechanism for joining them together to form a composite frame.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to claims of the disclosure that may afford certain benefits, under certain circumstances. However, other claims may also be preferred, under the same or other circumstances. Furthermore, the recitation of one or more preferred claims does not imply that other claims are not useful, and is not intended to exclude other claims from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise. The term "and/or" means one or all of the listed elements or a combination of any two or more of the listed elements.

Also herein, all numbers are assumed to be modified by the term "about" and in certain embodiments by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein, the term "room temperature" refers to a temperature of 20° C. to 25° C. or 22° C. to 25° C.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list.

DETAILED DESCRIPTION OF EXEMPLARY EMBODIMENTS

Figure 1A:
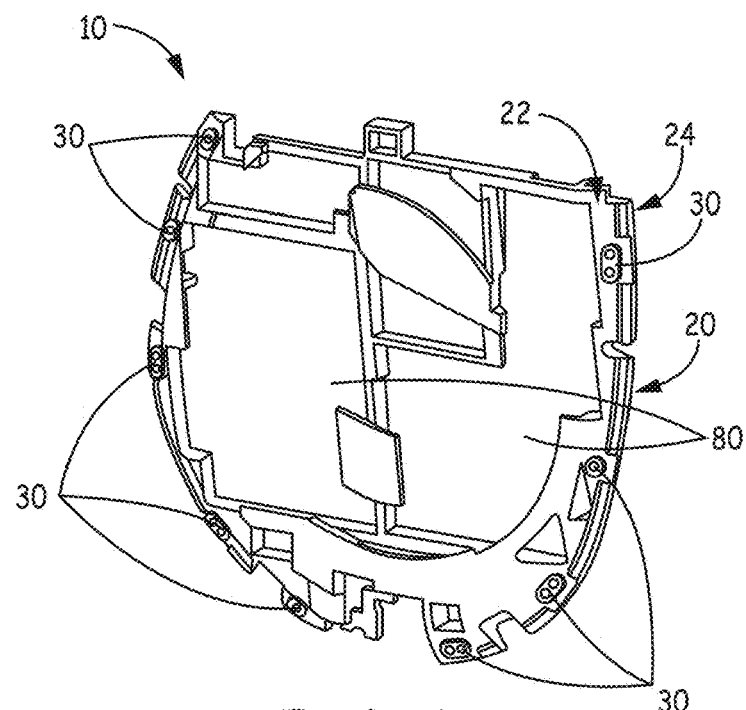
FIG. 1A is a perspective view of an exemplary frame.

The present disclosure provides an implantable medical device (IMD) that includes a housing configured to be sealed (e.g., hermetically sealed or otherwise), and a frame that provides structural rigidity and limits relative movement of the components within the IMD assembly. The exemplary IMD may include electronic components, such as a processor, circuit board, battery, or capacitors.

In one embodiment, the present disclosure provides an IMD that includes a housing defining an interior space; one or more components disposed in the interior space of the housing; and a frame disposed in the interior space of the housing. Preferably, the frame includes one or more first polymeric portions and one or more second polymeric portions coupled to the one or more first polymeric portions. In certain embodiments, at least one of (preferably, all of) the one or more first polymeric portions has a higher durometer than at least one of (preferably, all of) the one or more second polymeric portions. In certain other embodiments, at least one of (preferably, all of) the one or more first polymeric portions and at least one of (preferably, all of) the one or more second polymeric portions are of the same material. Also, the one or more second polymeric portions provides an interference fit between the one or more second polymeric portions and at least one of the housing and the one or more components disposed in the interior space of the housing.

In the following detailed description of illustrative embodiments, reference is made to the accompanying figures of the drawings which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary structures, assemblies, and methods shall be described with reference to FIGS. 1-5. It will be apparent to one skilled in the art that elements from one embodiment may be used in combination with elements of the other embodiments, and that the possible embodiments of such structures, assemblies, and methods using combinations of features set forth herein is not limited to the specific embodiments shown in the figures and/or described herein. Further, it will be recognized that the embodiments described herein may include many elements that are not necessarily shown to scale. Still further, it will be recognized that the size and shape of various elements herein may be modified but still fall within the scope of the present disclosure, although certain one or more shapes and/or sizes, or types of elements, may be advantageous over others. Various exemplary materials may be used within the exemplary structures, assemblies, and methods described herein. Also, any description of one first portion will be understood to apply to more than one first portion. Similarly, any description of one second portion will be understood to apply to more than one second portion.

Exemplary structures, assemblies, and methods for structural rigidity of an IMD and/or for preventing corrosion within the IMD are described herein. Generally, the exemplary structure includes a frame that may include multiple polymeric portions of different durometers. The frame, when positioned within the housing of an IMD may increase the stiffness of the assembled device (e.g., may provide robust mechanical fixation of the components within the device). The frame may provide the IMD stiffness through at least two polymeric portions that are coupled together (e.g., integrally molded in a multi-shot molding process, glued, adhered, intertwined with each other or otherwise joined together to form a composite frame). For example, a first polymeric portion (e.g., one or more first polymeric portions) may be formed of a rigid polymer and may be configured to provide structural rigidity to the frame, while a second polymeric portion (e.g., one or more second polymeric portions) may be formed of an elastomeric polymer that is deformable under a compressive force and may be configured to provide a compression fit of the components in the IMD assembly. The compression fit may limit movement of the components within the IMD with respect to each other.

The compression fit provided by the one or more second polymeric portions may be produced by an interference fit design (e.g., a designed interference resulting in the deformation of one or more components) of the elastomeric second polymeric portions with one or more components of the IMD, such as a circuit board, battery or housing. The interference fit design of the one or more second polymeric portions may also be configured to absorb assembly tolerances (e.g., variations in component dimensions), leading to a more mechanically stable, secure, and rigid assembly that is less likely to be damaged upon exposure to vibration or impact.

Materials

The first and second polymeric portions can be formed from thermoplastic or thermoset polymers. In certain other embodiments, at least one of (preferably, all of) the one or more first polymeric portions and at least one of (preferably, all of) the one or more second polymeric portions are of the same material, as described herein. In certain preferred embodiments, at least one of (preferably, all of) the first polymer portions has a higher durometer than at least one of (preferably, all of) the second polymeric portions. That is, at least one of the first polymeric portions is more rigid (i.e., higher durometer) than at least one of the second polymeric portions. Typically, the one or more first polymeric portions are formed of one or more thermoplastic polymers. Typically, the one or more second polymeric portions are formed of one or more elastomeric polymers, which may be thermoplastic or thermoset polymers. However, either of the first polymeric portions or the second polymeric portions may be formed of any suitable polymer, including thermoplastics or thermosets. In certain embodiments, the materials may be selected such that the first polymeric portion(s) are more rigid than the elastomeric (e.g., more elastic, resilient) second polymeric portion(s). In certain embodiments, the materials may be selected such that the first polymeric portion(s) and the second polymeric portion(s) are the same.

In certain embodiments, at least one of the first polymeric portion(s) has a higher durometer than at least one of the second polymeric portion(s). In certain embodiments, all of the one or more first polymeric portion(s) have a higher durometer than all of the one or more second polymeric portion(s).

The durometer is defined as a measure of the hardness of a material. The hardness is defined as a material's resistance to permanent indentation. The minimum durometer of the first polymeric portion(s) may be greater than 55D (Shore D), and the maximum durometer of the second polymeric portions may be less than or equal to 55D (Shore D). In certain embodiments, the durometer of the first polymeric portion(s) may be greater than or equal to 75D, or greater than or equal to 90D, or greater than or equal to 100 Rockwell R (not on the shore durometer "D" scale). In certain embodiments, the durometer of the second polymeric portion(s) may be less than or equal to 90A (Shore A), or less than or equal to 80A, or about 45A. In other embodiments the durometers may be based on the needs of a particular application and include combinations of the embodiments described above. The durometer values described herein are obtained using ASTM D 2240-05 (Standard Test Method for Rubber Property—Durometer Hardness).

Examples of suitable polymers for the first (preferably, more rigid) polymeric portion(s) include, but are not limited to, liquid crystalline polymers (such as poly-paraphenylene terephtalamide available under the trade name KEVLAR from DuPont, or a condensation polymer of 4-hydroxybenzoic acid and 6-hydroxynaphtahlene-2-carboxylic acid available under the trade name VECTRA from Celanese Corporation, Irving, Tex.), polyetherether ketone, polysulfone, polypropylene, polystyrene, acrylonitrile butadiene styrene copolymer, polycarbonate, polyvinyl chloride, poly(methyl methacrylate), polyphenol oxide, polyimide, polyamide, polymethylene oxide, polyurethane, polyurea, polyester, acrylonitrile-butadiene-styrene copolymer (ABS), or blends or copolymers thereof.

Suitable materials for the first (preferably, more rigid) polymeric portion(s) also include fiber reinforced polymers wherein the fibers include glass fiber, carbon fiber, liquid crystalline fiber, mineral fiber, carbon nanotube, metallic fiber, etc. The matrix polymer may include any of those listed above.

In one exemplary embodiment, the one or more first polymeric portion(s) are formed of a thermoplastic polymer such as polyetherether ketone (such as that available under the trade name INVIBIO from Invibio, United Kingdom), liquid crystalline polymers (such as poly-paraphenylene terephtalamide available under the trade name KEVLAR from DuPont, or a condensation polymer of 4-hydroxybenzoic acid and 6-hydroxynaphthalene-2-carboxylic acid available under the trade name VECTRA from Celanese Corp., Irving Tex.), polysulfone (such as that available under the trade name UDEL from Solvay, Houston, Tex.), polyimide (such as that available under the trade name ULTEM from Sabi, Riyadh, Saudi Arabia), polycarbonate, acrylonitrile-butadiene-styrene copolymer (ABS), or other engineering grade polymers, etc.

Examples of suitable polymers for the second (preferably, less rigid, more elastomeric) polymeric portion(s) include, but are not limited to, low density polyethylene, ethylene-propylene copolymers, ethylene-butadiene copolymer, ethylene-propylene-diene monomer (EPDM), polybutadiene, polyvinylacetate, nitrile-butadiene copolymer, polyisoprene, silicone, fluoropolymer, polyether, polyester, polycarbonate, polyurethane, polyether-polyurethane copolymer, polyester, and polyamide. Other suitable polymers include copolymers of such elastomers with other non-elastomeric polymers (e.g., urethane, amide, urea, styrene, acrylonitrile, etc.), plasticized polymers (such as plasticized polyvinyl chloride (PVC)), elastomer-glass polymer blends (such as nitrile-butadiene rubber/polyvinyl chloride blends (NBR/PVC blends), elastomer-crystalline polymer blends (such as EPDM/polypropylene (PP) blends available under the trade name SANTOPRENE from Exxon, Irving, Tex.).

In one exemplary embodiment, the one or more second polymeric portion(s) are formed of an elastomeric thermoplastic or thermoset such as silicone, EPDM, styrene-ethylene-butadiene-styrene copolymer (SEBS), and EPDM/PP blend. Preferably, the one or more second polymeric portions are formed of EPDM/PP blends (such as that available under the trade name SANTOPRENE from Exxon), or SEBS (such as that available under the trade name KRATON from Kraton Polymers, Belpre, Ohio).

Embodiments of FIGS. 1 and 2

Figure 1B:
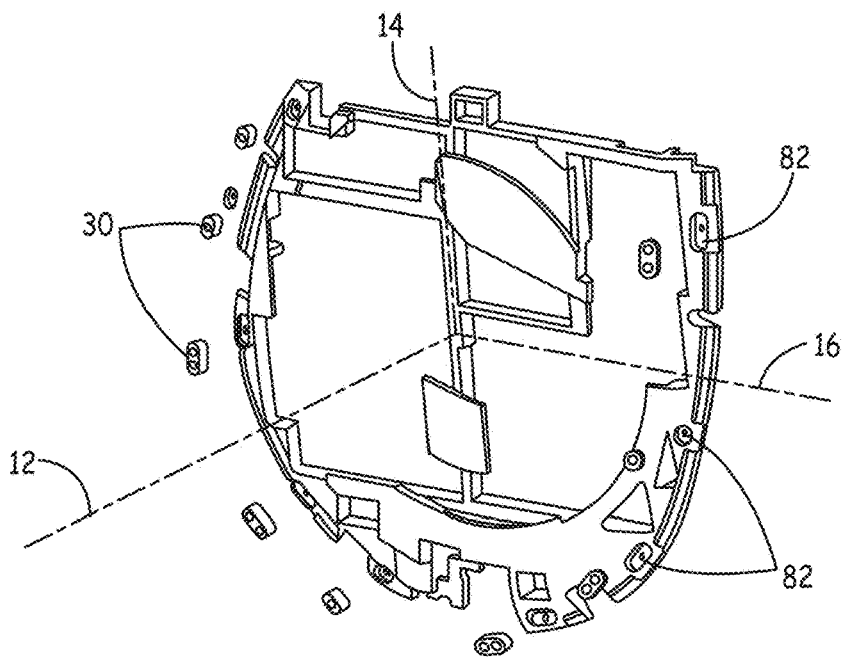
FIG. 1B is an exploded assembly view of the frame of FIG. 1A.
Figure 1C:
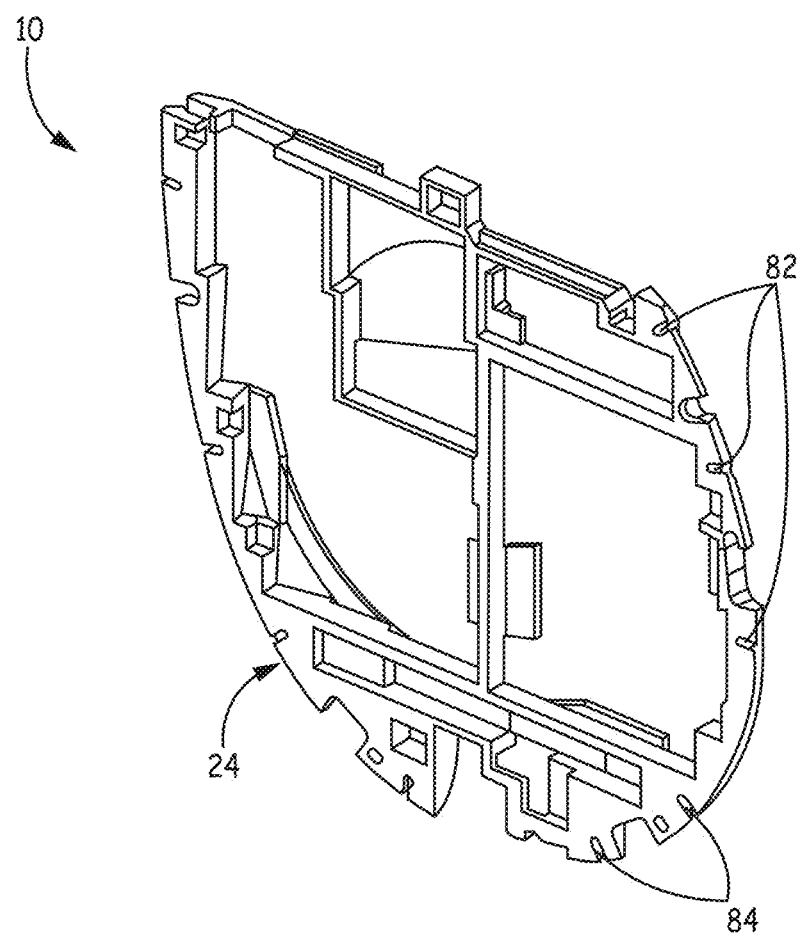
FIG. 1C is a bottom perspective view of the frame of FIG. 1A.
Figure 1D:
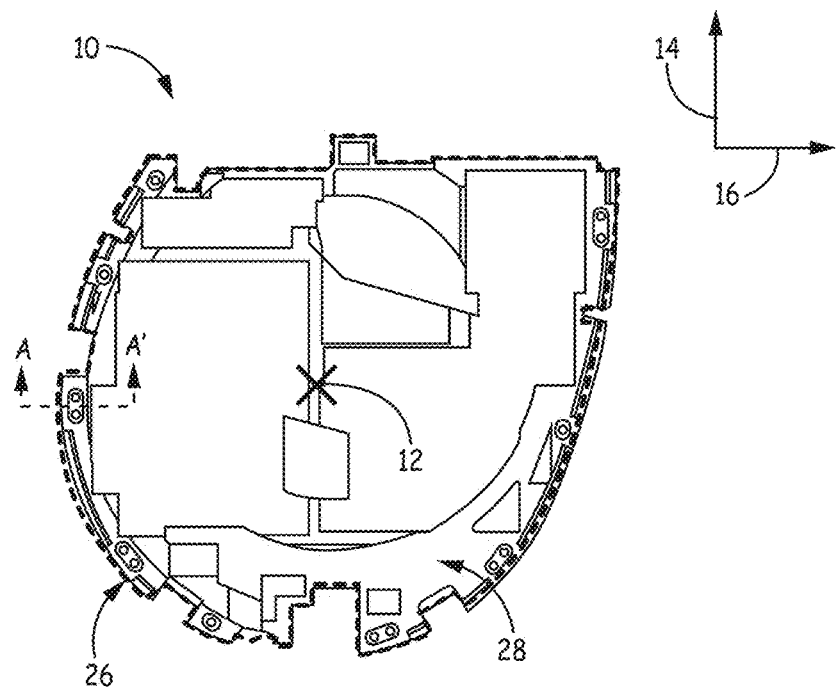
FIG. 1D is a top view of the frame of FIG. 1A.
Figure 1E:
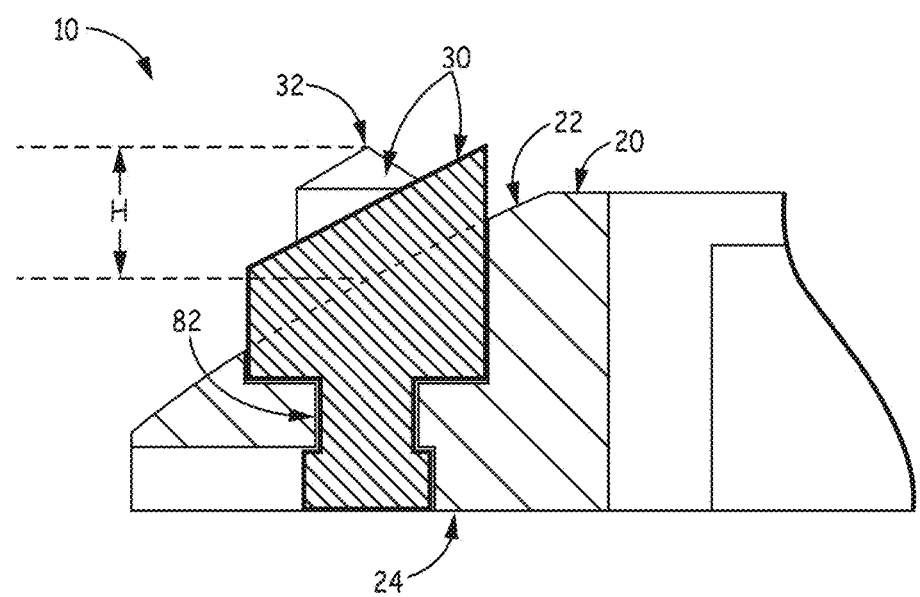
FIG. 1E is a cross sectional view of the frame of FIG. 1A taken along line A-A' in FIG. 1D.
Figure 1F:
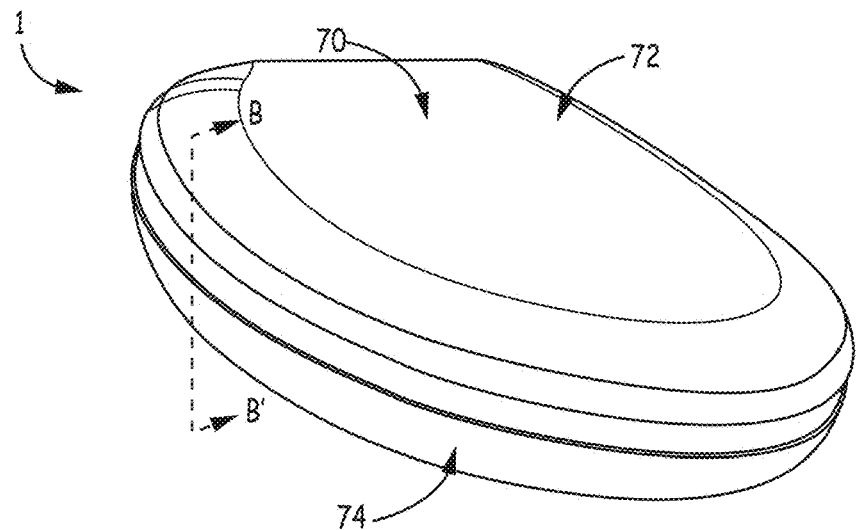
FIG. 1F is a perspective view of an exemplary assembled IMD including the frame of FIG. 1A.

Multiple views of an exemplary frame 10 (e.g., for increasing the structural rigidity) of an IMD assembly are depicted in FIGS. 1A-1H. It is noted that not every element is identified in every drawing of a particular embodiment, but rather the various drawings of an embodiment together form the disclosure as a whole. As shown in FIG. 1A-1D, the exemplary frame 10 may include a first polymeric portion 20 and one or more second polymeric portions 30. The first polymeric portion 20 of the frame 10 may be formed of or define a geometry such that the first polymeric portion 20 is configured to e.g., provide structural rigidity to an IMD 1 (FIGS. 1F-1H), to provide separation between internal components of the IMD 1, and to provide locating and retention features to other components within the IMD 1 when the IMD 1 is in the assembled state (FIG. 1F).

As depicted in FIG. 1A, the first polymeric portion 20 may include a first surface 22, and a second surface 24 opposite first surface 22. The distance from the first surface 22 to the second surface 24 defines a thickness or height of the first polymeric portion 20 (e.g., along an axis of assembly 12 (shown in FIG. 1B)). The first polymeric portion 20 may further include an outer perimeter 26 (FIG. 1D) including the exterior edges of the first polymeric portion 20 that are distal from the center of the first polymeric portion 20 and surround (e.g., define the bounds) of an inner portion 28. The first polymeric portion 20 generally lies in a frame plane (defined as the plane including axes 14 and 16, shown in FIG. 1B and FIG. 1D) that is perpendicular to the axis of assembly 12 (e.g., lying substantially within a plane perpendicular to the axis of assembly 12, or lying in a plane substantially perpendicular to the axis of assembly 12). As shown in the embodiment of FIG. 1D, the outer perimeter 26 is formed in a generally "closed horseshoe" shape.

The one or more second polymeric portions 30 may be contained within the outer perimeter 26 and be surrounded by the first polymeric portion 20 in the frame plane (plane through axes 14 and 16). In other words, the first polymeric portion 20 defines the outer perimeter 26 (as described above, shown in FIG. 1D), and the one or more second polymeric portions 30 are located within the bounds of the outer perimeter 26 and are not exposed to the outer perimeter 26.

Figure 1G:
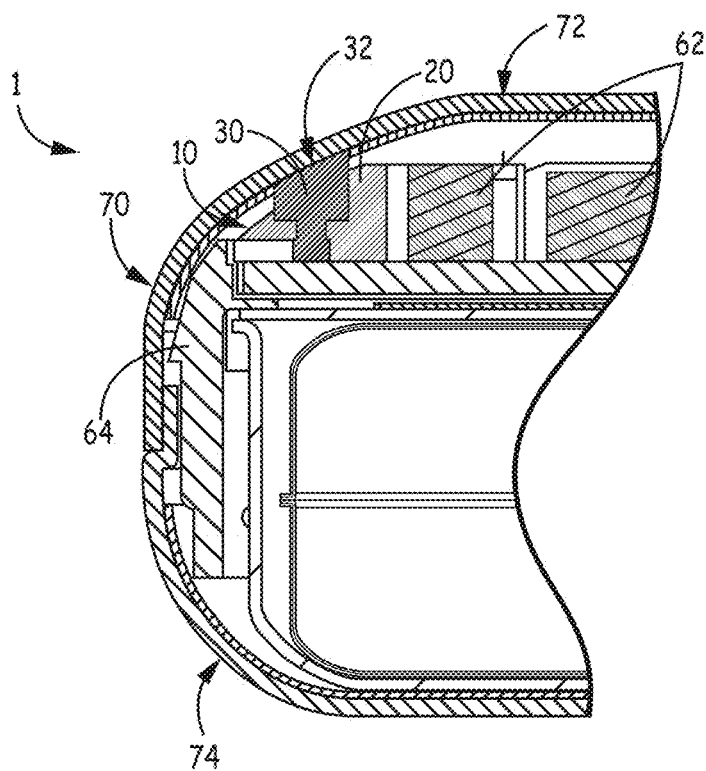
FIG. 1G is a cross sectional view of a portion of the exemplary IMD of FIG. 1F taken along line B-B' in FIG. 1F, including the frame of FIG. 1A.
Figure 1H:
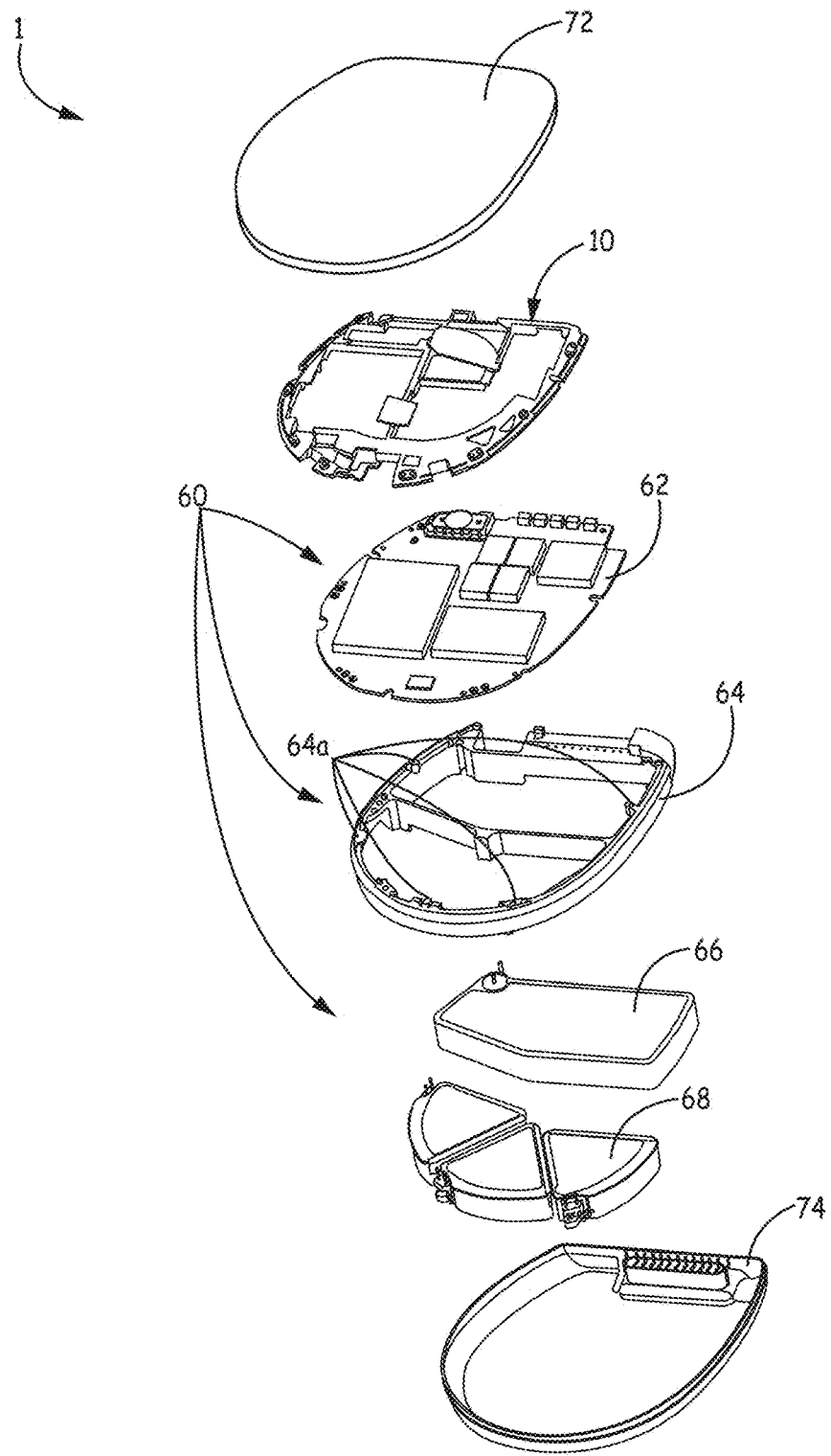
FIG. 1H is an exploded assembly view of the exemplary IMD of FIG. 1F.

In an exemplary embodiment, the first polymeric portion 20 may further include one or more openings 80 (FIG. 1A). Openings 80 (e.g., holes, apertures, cut outs) may be configured to accommodate at least a portion of another component of the IMD 1. For example, as shown in FIG. 1H, circuit and electronics 62 occupy at least a portion of the space within the one or more openings when assembled. In addition to allowing placement of other components in the openings 80, openings 80 may be configured to support, retain or locate components of the IMD 1, including electrical components.

In an exemplary embodiment, the first polymeric portion 20 may be formed from a thermoplastic polymer. The polymer may be a rigid polymer. In an exemplary embodiment, the first polymeric portion 20 is a rigid thermoplastic having a durometer of greater than 55D. In one or more embodiments, the first polymeric portion 20 may have a durometer of greater than or equal to 75D, or higher than 100 Rockwell R (a hardness that exceeds the shore "D" scale), depending on the particular application and the degree of rigidity that is required given the geometry of the frame and the expected forces to be induced on the device.

In order to couple the second polymeric portion (or portions) 30 to the first polymeric portion (or portions) 20 to form frame 10, the first polymeric portion 20 may include one or more aperture(s) 82 (FIGS. 1B, 1C, and 1E) extending through the first polymeric portion 20 from the first surface 22 to the second surface 24 (FIGS. 1A and 1E). To facilitate coupling of the second polymeric portion(s) 30 to the first polymeric portion(s) 20, apertures 82 may be formed as through-holes that capture the material of the second polymeric portion(s) 30 within the through-hole(s), an example of which is shown in FIG. 1E. In other words, aperture(s) 82 may be configured to capture the second polymeric portion(s) 30. Thus, aperture(s) 82 may form a portion of the coupling between the first polymeric portion(s) 20 and the second polymeric portion(s) 30. For example, at least one of apertures 82 may be configured such that at least a portion of the aperture 82 may be occupied by at least a portion of one or more of the second polymeric portions 30 (e.g., at least a portion of at least one of the one or more second polymeric portions 30 is located within at least one of the one or more apertures 82). Apertures 82 may also be completely filled by at least one of the one or more second polymeric portions 30. A cross section of an exemplary aperture 82 is shown in FIG. 1E.

In one or more embodiments, the one or more second polymeric portions 30 are integrally molded into the first polymeric portion 20. One or more aperture(s) 82 may serve to retain the second polymeric portions 30 by capturing and retaining a section of the second polymeric portions 30 within apertures 82. The second polymeric portions 30 may extend through all or a portion of apertures 82, from the first surface 22 (e.g., outer surface) to the second surface 24. In some embodiments, at least a portion of one or all of the second polymeric portions 30 extends beyond the first surface 22 of the first polymeric portion 20 (e.g., the first surface 22 that is adjacent, proximate, directly adjacent, coupled to the second polymeric portion 30) in a direction distal to second surface 24. Apertures 82 are also depicted in FIG. 1C as viewed from the bottom or second surface 24. FIG. 1C also depicts the injection molding path 84 that may be used to integrally mold the second polymeric portion(s) 30 onto first polymeric portion 20. The injection molding path 84 may be the path through the first polymeric portion 20 which the polymeric material that forms the second polymeric portion 30 could be delivered during the molding process.

Herein, any two first and second portions are coupled if they are connected even by intermediate components. Alternatively, they can be coupled directly, e.g., with adhesive. In the design of FIG. 1E, the second polymeric portion 30 is captured in the aperture 82 of the first polymeric portion 30. However, a second polymeric portion 30 (e.g., a bumper) could be glued to a surface of the rigid first polymeric portion 20 of the frame 10.

The one or more second polymeric portion(s) 30 of the exemplary frame 10 shown in FIGS. 1A-1H may be formed of an elastomeric polymer. The second polymeric portions 30 may be formed of a particular geometry, or be located such that the second polymeric portions 30 are designed to have an interference fit relationship with one or more surrounding components. In other words, when the IMD 1 is assembled, one or more of the second polymeric portions 30 may be compressed (e.g., deformed, displaced) to consume tolerance within the IMD 1 and tighten the IMD 1 assembly. The second polymeric portions 30 may be resilient such that the one or more second polymeric portions 30 are compressible under application of a force from an uncompressed state (e.g., free state) to a compressed state (e.g., assembled in the IMD state).

The interference fit of the second polymeric portions 30 with other components in the IMD 1 is configured to provide compression forces between components and limit relative movement between components of the IMD 1. Together with the first polymeric portion 20, the second polymeric portions 30 serve to stabilize the components of the IMD 1. The second polymeric portions 30 may absorb assembly tolerances and may provide a tight fit in nominal and light load conditions, while the first polymeric portion 20 provides structural rigidity and additional stability when larger deformation loads are encountered.

FIG. 1E depicts a cross section of the frame 10 of FIG. 1D as taken along line A-A'. As shown in FIG. 1E, the first polymeric portion 20 defines the first surface 22 (e.g., outer surface). The second polymeric portion 30 is labeled in two locations for clarity but may be a single piece. The portion of 30 that is hatched represents the portion of 30 that the cross sectional view is taken through, while the un-hatched and cone shaped portion of 30 lies beyond line A-A' along axis 14. The second polymeric portions 30 may include a contact surface 32 that is deformed or displaced by the interference fit of at least one of the one or more second polymeric portions 30 with other components in the assembled IMD 1 (as shown in FIG. 1G). The contact surface 32 may be located away from the first surface 22 of the first polymeric portion 20. The second polymeric portions 30 may include a geometry that decreases in cross sectional area (e.g., narrow, taper) as the second polymeric portions 30 extends away from the first surface 22 (e.g., may include a conical or pyramidal shape). The cross sectional area is defined as being taken in a plane parallel to the plane of the frame (FIG. 1D, 14, 16).

As depicted in FIG. 1F, the contact surface 32 may contact and be compressed by other component(s) within the IMD 1, or by the housing 70 (e.g., first housing portion 72, second housing portion housing 74). All or a portion of the contact surface 32 of the second polymeric portion 30 may be located closer to the first surface 22 when the first polymeric portion 20 is in the compressed state than when in the uncompressed state. As shown in FIG. 1E, a height H of the contact surface 32 may be defined between the contact surface 32 and the first surface 22 (e.g., the surface of the first polymeric portion 20 that is proximate, adjacent, or directly adjacent to the second polymeric portion 30 including contact surface 32). When at least one of the one or more second polymeric portions 30 is in the compressed state, at least a portion of the height is less than or equal to 90% of the height H when the at least one of the one or more second polymeric portions 30 is in the uncompressed state. The geometry of the first polymeric portion 20 may be modified to create the defined compressive force when compressed by the components of the IMD 1 assembly. Depending on the geometry, the materials and the application, in other embodiments, at least a portion of the height H of at least one of the one or more second polymeric portions in the compressed state may be less than 80% of the height H in the uncompressed state, may be less than 70% of the height H in the compressed state, may be less than 50% of the height H in the compressed state, or may be less than 25% of the height H in the compressed state, or may be less than 10% of the height H in the compressed state, depending on the level of compression desired and the material characteristics.

FIG. 1F depicts the IMD 1 in the fully compressed or assembled state. As shown in FIG. 1, the housing 70 (72, 74) provides a sealed enclosure defining an interior space. In the assembled state, the housing 70 may be hermetically sealed.

FIG. 1G is a cross sectional view of the exemplary IMD 1 of FIG. 1F taken along line B-B' in FIG. 1F, which depicts the exemplary frame 10 in the compressed state as assembled in the exemplary IMD 1. As shown, the portion of the second polymeric portion 30 that includes contact surface 32 is deformed or displaced under a compressive force in an interference fit with the first housing portion 72 and is therefore not clearly visible. In one or more exemplary embodiments, the contact surface 32 is compressed and deformed by an interference fit with the first housing portion 72. In some embodiments, the interference fit of the second polymeric portion 30 may be between the second polymeric portion 30 and a component of the IMD 1 other than the housing 70 (72, 74).

Second polymeric portions 30 may take on, or define a variety of geometric configurations. For example, as shown in FIGS. 1A and 1B, the second polymeric portions 30 may act like bumpers between second polymeric portions 30 and other components of the IMD to which they have an interference fit. The second polymeric portions 30 may be generally circular or elliptical in nature and be spaced around the first surface 22 of the first polymeric portion 20 near (e.g., proximate, adjacent) at least a portion of the perimeter 26. In the embodiment of FIG. 1A, the second polymeric portions 30 are not in contact with the perimeter and may be surrounded by the perimeter in the plane (14/16) of the frame 10. In other embodiments (such as the embodiment of FIG. 2A-2B to be described herein), alternate geometries, including second polymeric portions 230 having all or a portion of the second polymeric portion(s) 230 located external to the perimeter 226, may be provided. Combinations of such embodiments may also be provided.

Other components of the IMD 1 depicted in FIG. 1G include a secondary frame 64 (further shown in FIG. 1H). Frame 10 may rest on and be supported by, located or retained by secondary frame 64. Retention elements 64a may be provided on secondary frame 64 as shown in FIG. 1H for supporting, locating or retaining frame 10. When used together, frame 10 and secondary frame 64 may further enhance the structure of the IMD 1 in a compact design.

FIG. 1H depicts the frame 10 included in the IMD 1 assembly (exploded view) including the housing 70 formed from the first housing portion 72 and the second housing portion 74 (e.g., which together form an interior space of the housing 70 when assembled). The housing 70 is configured to be welded together or otherwise sealed (e.g., hermetically) during assembly of the IMD 1 after all the components of the assembly, including the frame 10 (and any other additional components that are shown or not shown), are placed inside and electrically or operably connected as necessary. In the exemplary embodiment of FIG. 1H, the IMD 1 includes the first housing portion 72, the frame 10, one or more components 60 (e.g., circuit and electronics 62, a secondary frame 64, a battery 66, capacitors 68), and the second housing portion 74. The one or more components 60 may include additional components not shown.

As assembled, frame 10 may reside in contact with secondary frame 64 (e.g., may be supported by or retained by secondary frame 64). Frame 10 may be located or positioned via locating or retention elements 64a on the secondary frame 64. Secondary frame 64 may be made of any suitable polymer, as described above with reference to the first and second polymeric portions 20, 30 of frame 10, or any other suitable polymer. Secondary frame 64 may or may not include a desiccant material or other additive.

Figure 2A:
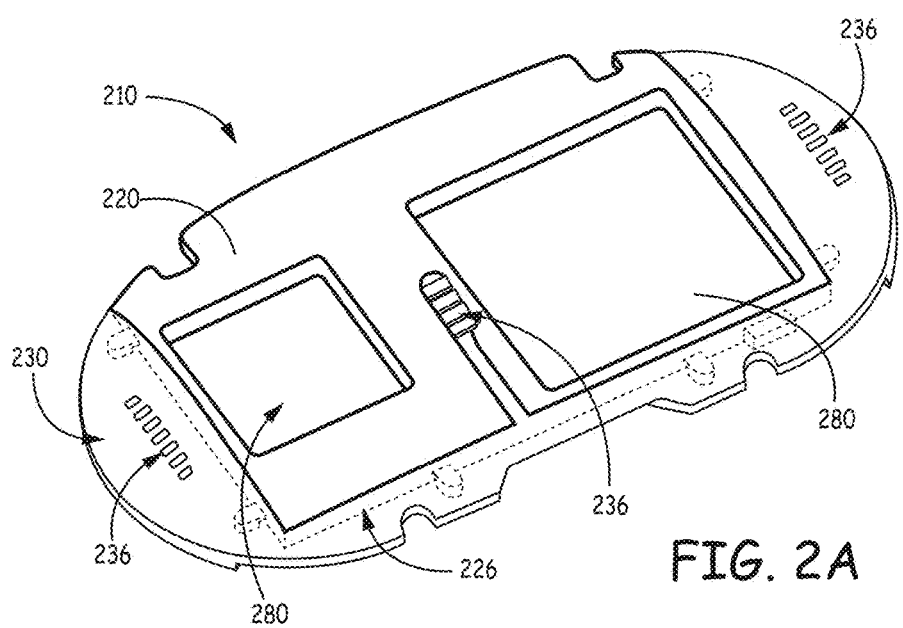
FIG. 2A is a perspective view of another exemplary frame.
Figure 2B:
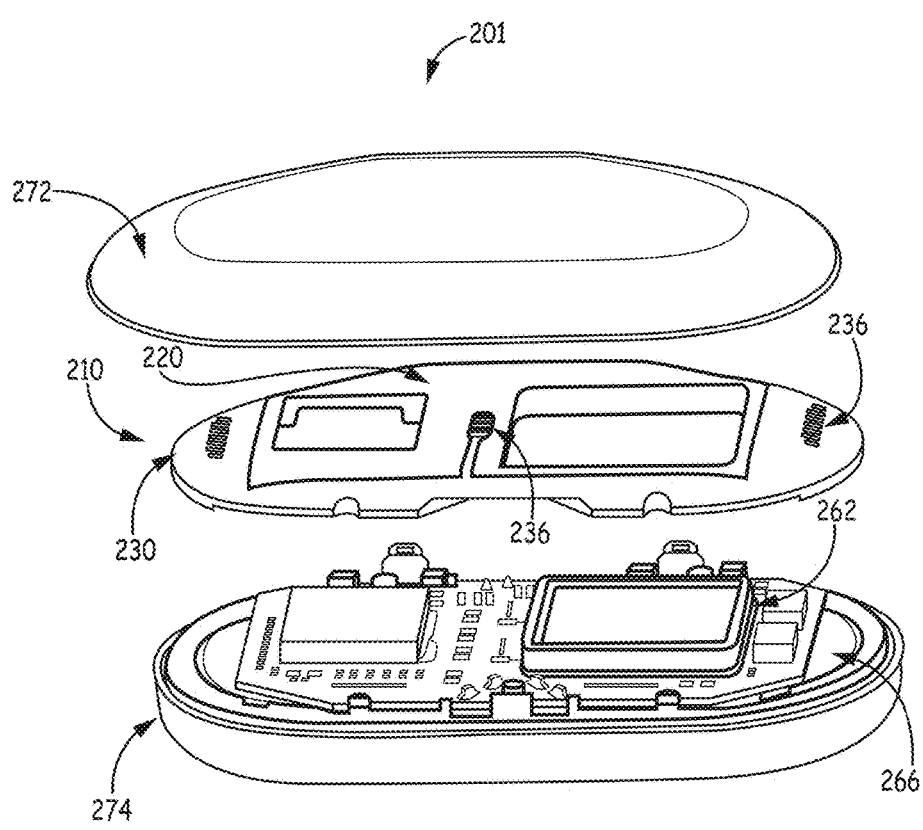
FIG. 2B is an exploded assembly view of an exemplary IMD including the frame of FIG. 2A.

Another exemplary frame 210 for increasing the rigidity of the assembled IMD 201 is depicted in FIGS. 2A-2B. Several features and/or portions of the exemplary frame 210 and IMD assembly 201 may be similar to the exemplary structures and systems described herein with reference to FIGS. 1A-1H, including methods of coupling. For example, the first polymeric portion(s) 220, the second polymeric portion(s) 230, other components of the IMD 201 (including but not limited to circuit and electronics 262, battery 266), the first and second portions of the housing 272, 274, the openings 280 and subcomponents or features thereof, may be similar to the first polymeric portion(s) 20, the second polymeric portion(s) 30, other components of the IMD 1 (including but not limited to circuit and electronics 62, battery 66), the first and second portions of the housing 72, 74, the openings 80, and subcomponents or features thereof (shown in FIGS. 1A-1H). As such, such features and/or portions may not be further described herein or are not described in the same level of detail, and it is to be understood that one or more of such features and/or portions may be used interchangeably between each and every embodiment described herein.

In one or more embodiments, the exemplary frame 210 may have other constructions without departing from the scope of the invention. FIGS. 2A-2B depict one of many possible designs for the frame 210, including a first polymeric portion(s) 220, and second polymeric portion(s) 230. It is noted that not every element is identified in every drawing of a particular embodiment, but rather the various drawings of an embodiment together form the disclosure as a whole.

In one or more exemplary embodiments, the first polymeric portion 220 defines the outer perimeter 226, and at least a portion of the one or more second polymeric portions 230 are coupled to the first polymeric portion 220 proximate (e.g., adjacent, directly adjacent, external to) to the outer perimeter 226.

As shown in FIG. 2A-2B, the second polymeric portion 230 may include protruding ribs 236. Protruding ribs 236 may be similar to and include any or all features related to the one or more second polymeric portions 30 and the contact surface(s) 32 of the embodiment of FIGS. 1A-1H. Protruding ribs 236 may be deformed (or reduced in height) in the compressed or assembly state as discussed with respect to the contact surface 32 of the embodiment of FIGS. 1A-1H, and/or include contact surface 32. Protruding ribs 236 may be present on any one or more surfaces of the second polymeric portions 230 in order to facilitate an interference fit with one or more components of the IMD 201 (e.g., in the same or similar manner as discussed with respect to the embodiment of FIGS. 1A-1H). The protruding ribs may include any or all of the height features described in relation to contact surface 32 including deformation, compression and height characteristics. In one or more embodiments, the protruding ribs 236 may have an interference fit relationship with the first housing portion 272, the battery 266, or any other component of the IMD 201 assembly.

Protruding ribs 236 may further be located on the second polymeric portion 230 proximate (e.g., adjacent, near) the outer perimeter 226 of the first polymeric portion 220, within the outer perimeter 226, or at a location external to (e.g., distal, not in contact with) the outer perimeter 226. The second polymeric portion 230 may be of generally planar shape (e.g., substantially planar, flat, including a thickness) and may surround at least a portion of the perimeter 226 of the first polymeric portion 220. For example, as shown in FIG. 2A the second polymeric portion 230 is a generally E-shaped geometry connected to 3 sides of the perimeter 226 with a portion extending into the center of the first polymeric portion 220. The protruding ribs 236 of second polymeric portions 230 may decrease in cross sectional area (e.g., narrow, taper), where the cross sectional area is taken in plane parallel to the plane of the frame (as shown in related FIG. 1D, 14, 16).

FIG. 2B depicts an IMD 201 assembly including the frame 210 of FIG. 2A. In one or more embodiments, the second polymeric portion 230 may be compressed between two components of the IMD 201. In the depicted embodiment, the second polymeric portion 230 that is external to the outer perimeter 226 is compressed between the first housing portion 272 and the battery 266. While the second polymeric portion 230 near the center of the first polymeric portion 220 is compressed between the first housing portion 272 and the circuit and electronics 262.

Desiccants and Other Additives

In some embodiments, either the first polymeric portion (20/220) or the second polymeric portion (30/230) of the frame (10/210) may include a desiccant material to provide moisture absorption capabilities and prevent corrosion of electronic components. For example, a desiccant material capable of absorbing moisture may be included in a polymer as described herein in a desirable manner, such that the tendency to absorb moisture during the manufacturing process is limited, while maintaining sufficient moisture absorption capabilities after the IMD (1/201) has been assembled and sealed (e.g., hermetically sealed).

In some embodiments, one or more desiccants may be molded into the first polymeric portion(s) (20/220) and/or the second polymeric portion(s) (30/230). Preferably, the second polymeric portion(s) (30/230) of the frame may include a desiccant material, but not the first polymeric portion(s), at least because inclusion of desiccants may undesirably weaken the rigid first polymeric portion(s).

A wide variety of suitable desiccants may be incorporated into (e.g., embedded, impregnated, etc.) the one or more polymers of any portion of the frame (10/210). Examples of desiccants that may be employed include calcium oxide, silica gel, activated alumina, clay, other natural zeolites, anhydrous magnesium, calcium sulfate, starches, molecular sieves, aluminosilicates, polyanhydrides, or any other suitable desiccant material. In one or more embodiments, the desiccant may include molecular sieve.

The desiccant may be combined with a wide variety of suitable (carrier or matrix) polymeric materials for producing the first polymeric portion(s) 20 and/or the second polymeric portion(s) 30. Thermoplastic or thermoset polymers, including but not limited to, those described above. The desiccant(s) and the polymer(s) may be blended, mixed, or included via any suitable process or method before or after molding so that the desiccant is included, added, embedded, or impregnated in the polymer(s). In one or more embodiments, the desiccant material is melt-blended into the polymers.

Any suitable amount of polymer and desiccant may be used. The more desiccant that is used in the blends, the higher the moisture absorption capacity the blends have and more rigid and/or brittle the materials are. The optimized desiccant amount depends on the balanced requirements of moisture absorption and mechanical integrity. In one exemplary embodiment, and as shown in Table 1, the composite was made with SANTOPRENE 8281-45MED polymer and molecular sieve desiccant powder (Type 3A, UOP, a Honeywell Company, NJ). In theory, moisture absorption capacities are proportional to the amount of desiccant compounded. Calculated capacities are listed in Table 1 where the moisture absorption capacity of pure desiccant was 25 wt % (based on the dry solid). A compound with 45% desiccant has a theoretical moisture absorption capacity of 112.5 milligrams of moisture per gram of compound. Moisture absorption capacity can be measured by placing a dried compound into an environment with a specific relative humidity and measuring the weight gain of the compound at the time of saturation. For example measured capacity was about 80 mg of moisture per gram of compound that contained 45 wt % desiccant (UOP 3A). The measurement was done by first drying the compound then placed it in a chamber with about 43% relative humidity at room temperature. The capacity can also depend on the polymers used in the compounds and the relative humidity of the environment where measurement is performed.

In one or more embodiments, a mixture of desiccant and polymer (i.e., matrix polymer) for purposes of molding may include at least 5 wt % desiccant and 95 wt % polymer. The mixture of desiccant and polymer may have up to 60 wt % desiccant and 40% polymer. If more than one desiccant or polymer is used, the weight percent of the polymer may be the cumulative weight percent of all the polymers and the weight percent of the desiccant may be the cumulative weight percent of all the desiccants.

TABLE 1

Capacity of moisture absorption as a function of desiccant powder loading

| Composition wt % of composite wt % thermoplastic elastomer | wt % desiccant powder (dry) | Theoretical moisture absorption capacity (mg moisture per gram of composite) mg moisture/g composite | Measured measured |
|---|---|---|---|
| 0 | 100 | 250 | |
| 10 | 90 | 225 | |
| 25 | 75 | 187.5 | |
| 40 | 60 | 150 | |
| 55 | 45 | 112.5 | 80 |
| 60 | 40 | 100 | |
| 75 | 25 | 62.5 | |
| 90 | 10 | 25 | |
| 100 | 0 | 0 | |

Moisture absorption rates of compounds depend on the moisture permeation rate of the matrix polymers. Those polymer matrices with higher moisture permeation rates allow for faster moisture absorption. Glassy and crystalline polymers have lower moisture permeation rates than rubbery polymers. Among the rubbery polymers, silicone rubber usually has a higher permeation rate. Therefore, silicone/desiccant compounds usually have faster moisture absorption rates than other compounds. Rubbery or elastic compounds usually have faster moisture absorption rates than glassy or crystalline compounds. The moisture absorption rate can be measured by experimentation. For example, a compound is pressed or injection-molded into a regular sheet. Moisture absorption rates can be assessed by placing a dried sheet in an environment with fixed relative humidity and temperature and monitoring the weight of the samples over time until reaching saturation. In one or more embodiments, the desiccant material is preferably mixed into relatively slow moisture absorbing carrier polymer such as EPDM/PP blend, SEBS, or any other suitable polymer discussed herein. In other embodiments, the desiccant may be mixed into combined carrier polymers that have fast and slow moisture permeation rates.

The rate at which the carrier polymer absorbs moisture is an important material characteristic. Traditionally, in the use of relatively quick moisture absorbing carrier polymers, such as silicone, manufacturing time and humidity conditions are limited. In order to prevent a desiccant embedded in a relatively quick moisture absorbing carrier polymer from absorbing moisture too quickly during the manufacturing process, both manufacturing time and humidity conditions may be controlled. If too much moisture is absorbed during the manufacturing process, less moisture absorbing capacity is available after the IMD 1 has been assembled and sealed.

In one or more embodiments, the desiccant is embedded in the relatively slow moisture absorbing carrier polymer. Embedding the desiccant in the relatively slow moisture absorbing carrier polymer permits the working "open time" (e.g., assembly time, manufacturing time) to be extended and the total capacity during "closed time" (e.g., after being sealed) to be drastically improved. In other words, by reducing the rate at which the desiccant is able to absorb moisture, the amount of moisture the desiccant absorbs during an assembly process of the same time may be reduced. Alternatively, a longer time may be permitted for the assembly process to be completed before the desiccant has absorbed too much moisture. The working conditions (e.g., humidity level) may also be able to be more variable without any substantial change in the desiccant moisture capacity of the sealed IMD 1.

Decreasing the amount of moisture absorbed during the assembly process improves the remaining capability of the desiccant to absorb moisture once the IMD 1 is assembled. Since the desiccant retains a higher capacity to absorb moisture after the IMD 1 is assembled, the desiccant amount or volume may be reduced, or a desiccant of the same volume may function as a more effective desiccant. This is further described with reference to FIG. 3A and FIG. 3B.

Figure 3A:
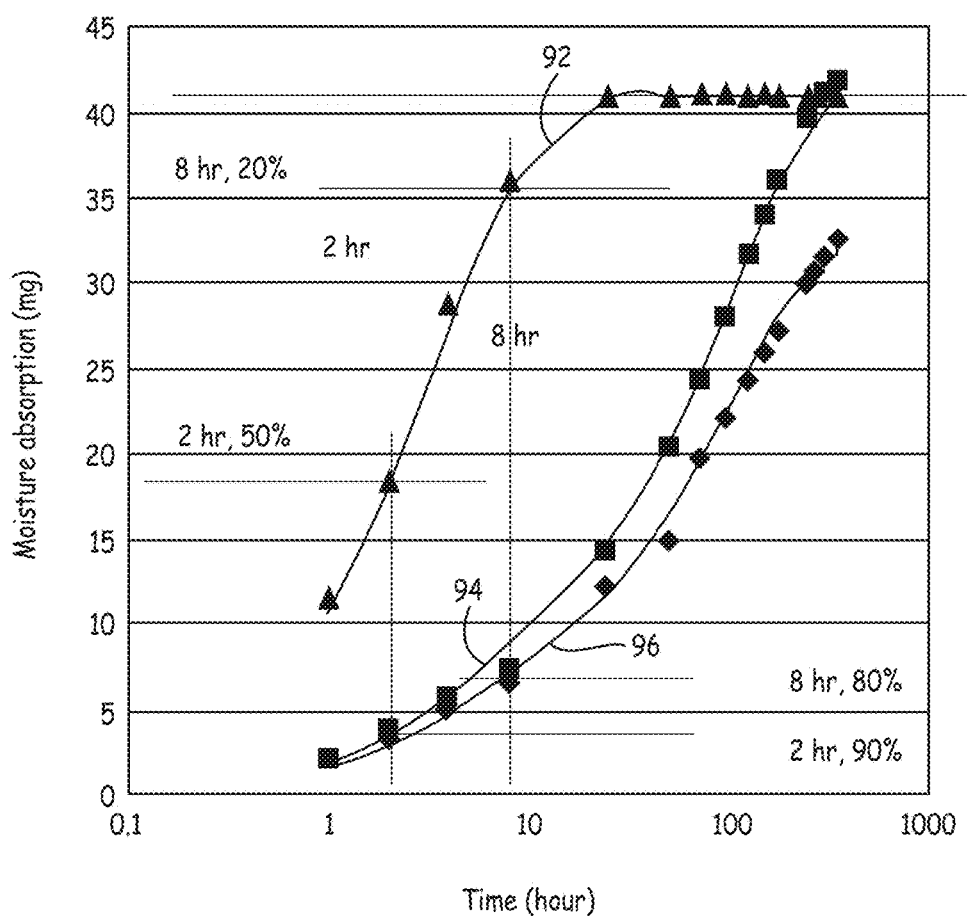
FIG. 3A is a graph of exemplary moisture absorption rates of various polymeric desiccants.

FIG. 3A depicts a sample comparison of moisture absorption take up rates of a thermoplastic elastomer EPDM/PP (SANTOPRENE, a blend of EPDM and PP) mixed with desiccant (UOP type 3A molecular sieve) versus a thermoset liquid silicone rubber (LSR available from Dow Corning) mixed with desiccant (UOP type 3A molecular sieve). The thermoset liquid silicone rubber and desiccant mixture (55/45 wt %) was formed into a component ("Part 92") shown in FIG. 3B. The thermoplastic EPDM/PP and desiccant mixture (55/45 wt %) was formed into a component ("Part 94") shown in FIG. 3B. Parts 92 and 94 each have a size roughly 1 inch by 1 inch by 0.040 inch and the same geometries.

Figure 3B:
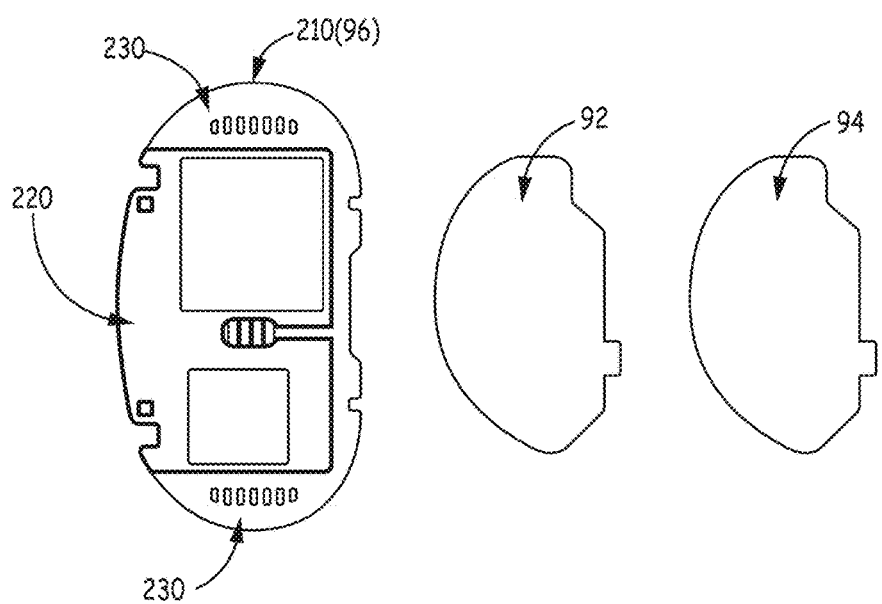
FIG. 3B is a top view of the components tested in FIG. 3A, including the exemplary frame of FIG. 2A.

Referring to FIG. 3B, Part 94 and portions of Part 96 (210) are made of the EPDM/PP and desiccant mixture described above. The geometry of Part 96 (210) is reflective of the geometry embodiment of frame 210, as defined in FIGS. 2A and 2B. Part 96 (210) includes first polymeric portion 220 made of a rigid polymer (without desiccant) and second polymeric portion 230 made of EPDM/PP and desiccant (as described above and in common with part 94). The parts 92, 94, 96 were dried by baking them in a vacuum oven at 90 degrees Celsius (° C.) for at least two days. They were placed in a chamber with 43% relative humidity (RH) at room temperature. The weight gains due to moisture absorption were tracked with a microbalance. Part 92 (silicone/desiccant) absorbed moisture faster, and reached 50% moisture absorption capacity within 2 hours and 80% capacity within 8 hours. Parts 94 and 96, made of EPDM/PP and desiccant, absorbed moisture more slowly, reaching 10 and 20% capacities, respectively, within the same times. This is graphically illustrated in FIG. 3A.

Moisture absorption is a permeation-absorption controlled process, i.e. moisture permeates through the carrier polymer (i.e., the matrix polymer) and is absorbed into the desiccant embedded inside. The moisture absorption rate depends, at least in part, on geometry of the parts. For example, smaller samples have faster absorption rates. A general rule of thumb is that absorption rate becomes 4 times faster when the part size is reduced by half. The part size can be the smallest dimension if it is a regular shape (e.g., rectangular). Also, the moisture absorption rate depends, at least in part, on temperature. For example, at room temperature after being tested for 2 hours, the silicone part (Part 92) had 50% absorption and the EPDM/PP part (Part 94) had 10% absorption. The moisture absorption rate of the silicone part (Part 92) was about 5 times faster than that of the EPDM/PP part (Part 94). After the same absorption duration, at 37° C., the moisture absorption rate of the silicone part (Part 92) was about 4 times faster than that of the EPDM/PP part (Part 94). At 70° C., the moisture absorption rate of the silicone part (Part 92) was about 2 times faster than that of the EPDM/PP part (Part 94).

In one or more embodiments, the preferred materials for use in the one or more second polymeric portion(s) (30/230) may absorb 0.1-300 milligrams of moisture per gram of the polymer including the desiccant material and 0.1 to 300 hours exposure to 0-70% relative humidity at room temperature as discussed herein. In one or more embodiments, the preferred materials for use in the one or more second polymeric portion(s) (30) may absorb 50-120 milligrams of moisture per gram of the polymer including the desiccant material at 200 hours exposure to 20-50% relative humidity at room temperature as discussed herein.

In one or more embodiments, other additives may be added to the polymeric materials of the first polymeric portion(s) (20/220) and/or the second polymeric portion(s) (30/230). In one or more embodiments, an additive such as activated carbon or activated charcoal, or any other suitable sorbent (e.g., potassium permanganate), may be blended into the polymeric material. Suitable sorbents may be finely divided materials that are capable of absorbing a harmful gas, and which typically has a surface area of greater than 100 m$^2$/g. Such sorbents may be present with or without the desiccant. The resulting composite material may absorb (e.g., retain, contain, control) inorganic molecules such as sulfur or sulfur-containing compounds (e.g., $H_2S$ or $SO_2$), or organic contaminants such as small molecular weight organic contaminants that may not be compatible with other components of the device (e.g., volatile battery electrolyte solvents such as carbonates, dimethoxyethane, and the like). For example, a presence of sulfur may accelerate the corrosion of copper wire in circuitry. Including both a desiccant and activated carbon may provide removal of both moisture and organic/inorganic contaminants. The amount of activated carbon or other sorbent is typically within a range of 5-45 wt %, based on the total weight of compounds. For example, polymer, desiccant, and activated carbon can be in a range of 90:5:5 to 50:25:25, or 50:5:45, or 50:45:5

In other embodiments, palladium- or platinum-coated titanium particulates may be used as a hydrogen gas sorbent to keep the hydrogen partial pressure in the device-interior atmosphere very low. Elevated levels of hydrogen inside hermetically sealed electronic devices may be created by outgassing from conductors electro-plated with gold or by electrochemical reactions inside of devices components such as batteries or capacitors. Such elevated hydrogen partial pressures are known to have the potential to create malfunction of integrated circuit components such as resistors or ceramic capacitors (P. Schuessler and D. Feliciano-Welpe, "The Effects of Hydrogen on Device Reliability," *Hybrid Circuit Technology*, 8, pp. 19-26 (1991)). Palladium-coated titanium is used because titanium is known for its large capacity for hydrogen storage and the palladium coating prevents the passivation of titanium by atmospheric gases such as oxygen and water vapor. Furthermore, palladium is known to have a very high diffusivity for hydrogen (R. Kullberg, H. Florence, M. Moraja, R. Petersen, "Getters for Microlectronic Packages," *Advanced Packaging*, 13(12), pp. 30-33, (2004)). Hence, these materials are able to absorb and contain hydrogen inside of the hermetically sealed devices. The amount of such hydrogen gas sorbents may be 10-50 wt %, based on the weight of the polymer and sorbent.

In one or more embodiments, the sorbent may be an amine- and/or ammonia-absorbing chemical. Such sorbents may be used to minimize the amine or ammonia release from the epoxy used inside an IMD. Amine- and/or ammonia-absorbing chemicals include, but not limited to, clay, zirconium phosphate, etc. The amount of such sorbent may be 10-50 wt %, based on the weight of the polymer and sorbent.

Also, zirconium oxide can be used to absorb acidic chemicals.

If a sorbent chemical is volatile, the sorbent chemicals may be immobilized with a second additive, and both may be added into the carrier (i.e., matrix) polymers. For example, clay can be used as a second additive for hydrophobic sorbent chemicals that can absorb wax or processing additives in other polymer components.

In one or more embodiments, a radiopaque filler material such as $BASO_4$, tungsten, tungsten carbide, tantalum, or any other suitable material, may be compounded into either or both of the first polymeric portion(s) (20/220) and/or the second polymeric portion(s) (30/230). Inclusion of a radiopaque material provides the ability to determine the presence of the first polymeric portion(s) (20/220) and/or second polymeric portion(s) (30/230) under x-ray. In other embodiments, the radiopaque material may be in the form of a marker molded into the first polymeric portion(s) (20/220) and/or the second polymeric portion(s) (30/230).

In one or more embodiments, in addition to mechanical damping and/or moisture absorption capabilities, it is also desirable for either the first polymeric portion(s) (20/220) or second polymeric portion(s) (30/230) to act as a heat sink for preventing excessive heating of the IMD 1, including the housing during a welding or housing closure process. Materials that function as heat sinks include crystalline polyethylene, crystalline polypropylene, crystalline polyethylene oxide, etc. The melting points of the crystalline polymers should be the highest temperature allowed for the devices. Higher crystallinity is preferred.

In certain embodiments of the present disclosure, a preferred combination of materials for the second polymeric portion(s) (30/230) includes an SEBS thermoplastic elastomer available under the trade names KRATON D2109 (Durometer 46A) and G2705 (Durometer 57A), mixed with a molecular sieve powder desiccant (available under the trade name UOP Type 3A from Honeywell, Morris Plains, N.J. The composition may include a weight ratio of amounts of SEBS to molecular sieve in a range of 95:5 to 40:60.

In certain embodiments of the present disclosure, a preferred combination of materials for the second polymeric portion(s) (30/230) includes an EPDM/PP thermoplastic elastomer blend available under the trade names SANTOPRENE 8281-35MED (Durometer 35A), 8281-45MED (Durometer 45A), 8281-75MED (Durometer 75A), mixed with a molecular sieve powder desiccant (available under the trade name UOP Type 3A from UOP, Honeywell, Morris Plains, N.J.). The composition may include a weight ratio of amounts of EPDM/PP to molecular sieve in a range of 95:5 to 40:60 (preferably, in a range of 55:45 to 50:50).

In certain embodiments of the present disclosure, a preferred combination of materials for the second polymeric portion(s) includes (30/230) thermoplastic polyether-polyurethane copolymer elastomer available under the trade name ELASTHANE 80A from DMS, Netherlands (Durometer 80A), mixed with a molecular sieve powder desiccant (available under the trade name UOP Type 3A). The composition may include a weight ratio of amounts of ELASTHANE 80A to molecular sieve in a range of 95:5 to 40:60.

In certain embodiments of the present disclosure, a preferred combination of materials for the second polymeric portion(s) includes a crystalline polyethylene (PE) polymer mixed with a molecular sieve powder desiccant (available under the trade name UOP Type 3A). The composition may include a weight ratio of amounts of crystalline PP to molecular sieve in a range of 90:10 to 50:50.

In certain embodiments of the present disclosure, any of the above-described preferred combinations may also include $BASO_4$, tungsten, tungsten carbide, tantalum, etc. for radiopacity. The compositions may include a weight ratio of amounts of polymer to molecular sieve to radiopaque filler in a range of 75:5:20 to 40:40:20.

In certain embodiments of the present disclosure, any of the above-described preferred combinations may also include a sorbent material having organic chemical absorption capabilities, particularly activated carbon. The compositions may include a weight ratio of amounts of polymer to molecular sieve to activated carbon in a range of 90:5:5 to 50:25:25, or 50:5:45, or 50:45:5.

Methods of Making

Polymers and fillers can be compounded with many ways, for example, melt mixing with twin screw extruder, single screw extruder, batch mixer, solvent mixing, reactive mixing (mix monomers that polymerize into the polymers and the fillers, then do polymerization), and solid powder mixing. Mixing procedures and conditions can be developed by experts in the fields.

The exemplary embodiments of frames (10, 210) for use in an IMD (1, 201) may be manufactured and assembled in any suitable manner. An exemplary method for manufacturing the frames (10, 210) is described herein. Additional steps, fewer steps, or different steps may be included in the method without departing from the scope. An injection molding process, or any other suitable processing method may be used, including a 2-shot or integral molding process. The molding process may include one or more molds (e.g., sets of molds, mold portions). A molding process including more than 2-shots may also be used.

In one embodiment, a method includes: providing a housing defining an interior space; providing one or more components; providing one or more first polymeric portions; coupling one or more second polymeric portions to the one or more first polymeric portions to form a frame; inserting the one or more components and the frame into the interior space of the housing; and closing the housing, providing an interference fit between the one or more second polymeric portions and at least one of the housing and the one or more components. At least one of the one or more first polymeric portions has a higher durometer than at least one of the one or more second polymeric portions. Preferably, all of the first polymeric portions have a higher durometer than all of the second polymeric portions.

Figure 4:
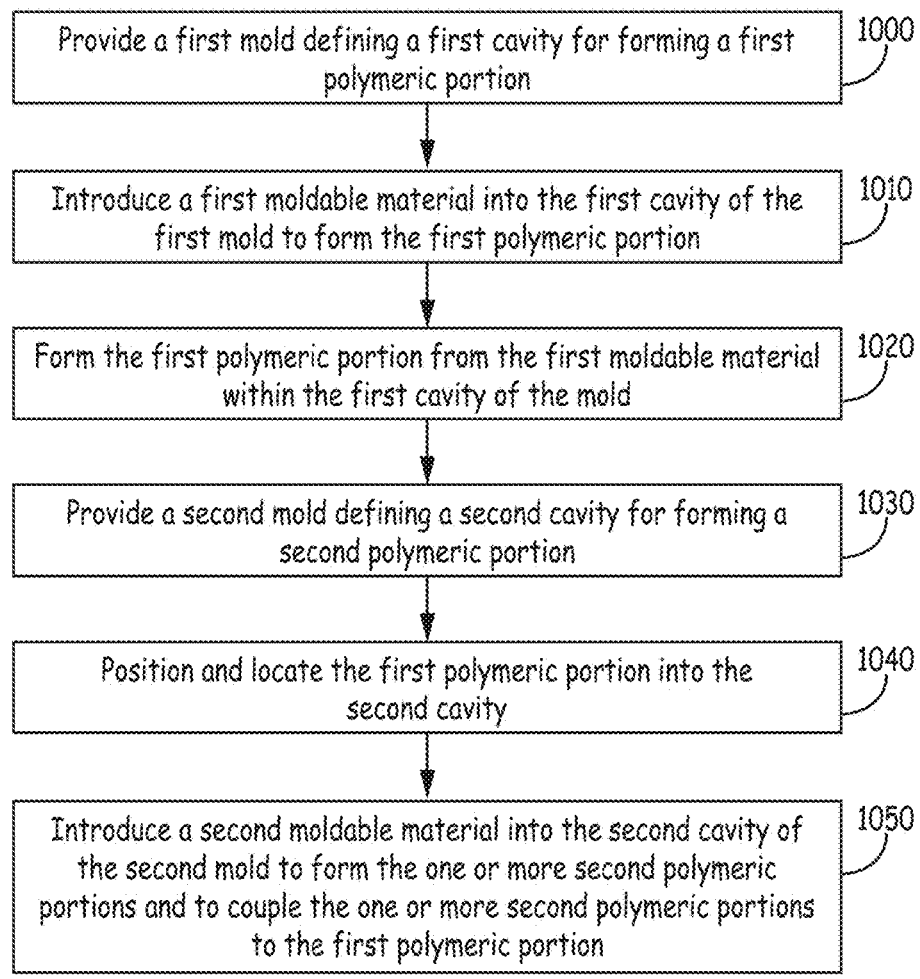
FIG. 4 is a flow chart of a method of making the frames of FIG. 1A or FIG. 2A.

As shown in FIG. 4, an exemplary method for forming frames (10, 210) may include providing a first mold defining a first cavity for forming a first polymeric portion (20, 220, step 1000), introducing a first moldable material into the first cavity of the first mold to form the first polymeric portion (20, 220, step 1010), forming the first polymeric portion (20, 220) from the first moldable material within the first cavity of the mold (step 1020), providing a second mold defining a second cavity for forming a second polymeric portion (30, 230, step 1030), positioning the first polymeric portion (20, 220) into the second cavity (step 1040), and introducing a second moldable material into the second cavity of the second mold to form the one or more second polymeric portions and couple the one or more second polymeric portions to the first polymeric portion (step 1050). In one or more embodiments, a portion of the first mold and a portion of the second mold may be the same. In other words, the molding process may be an automated single-cycle 2-shot molding process with one stationary half of the mold, and one rotating mold. The rotating half of the mold may change between step 1000 and step 1030. Alternatively, in some embodiments the 2-shot process may use completely different molds between step 1000 and step 1030, the first and second molds sharing no common portions.

Figure 5:
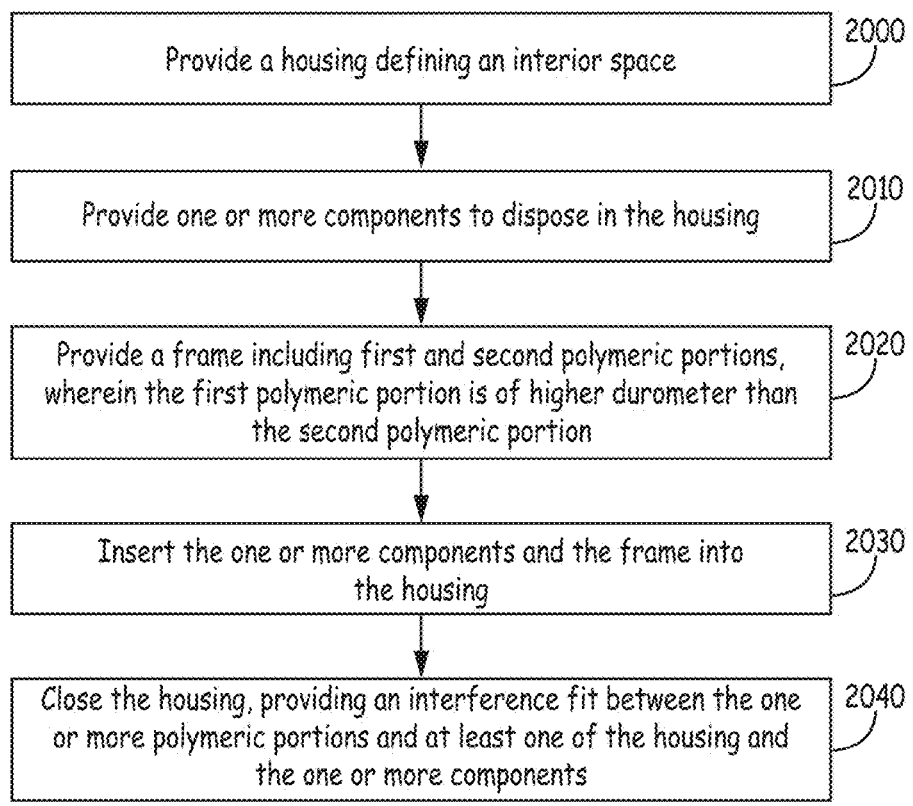
FIG. 5 is a flow chart of a method of assembling the IMD of FIG. 1H or FIG. 2B.

As shown in FIG. 5, an exemplary method of assembling an IMD (1, 201) including the frame (10, 210) produced by the process described herein, may include providing a housing (70, 270) defining an interior space (step 2000), providing one or more components (60, 260) to be disposed within (e.g., inserted into, placed within) the housing (70, 270, Step 2010), providing a frame (10, 210) including first and second polymeric portions (20, 30; 220, 230), the first polymeric portion (20, 220) being of a higher durometer than the second polymeric portion (30, 230, step 2020), inserting the one or more components (60, 260) and the frame (10, 210) into the housing (70, 270, step 2030), and closing the housing (70, 270), providing an interference fit between the one or more second polymeric portions (30, 230) and at least one of the housing (70, 270) and the one or more components (60, 260, step 2040).

Illustrative Embodiments

Embodiment 1 is an implantable medical device comprising:
a housing defining an interior space;
one or more components disposed in the interior space of the housing;
a frame disposed in the interior space of the housing, wherein the frame comprises:
one or more first polymeric portions; and
one or more second polymeric portions coupled to the one or more first polymeric portions;
wherein at least one of the one or more first polymeric portions has a higher durometer than at least one of the one or more second polymeric portions; and
wherein the one or more second polymeric portions provides an interference fit between the one or more second polymeric portions and at least one of the housing and the one or more components disposed in the interior space of the housing.

Embodiment 2 is the device of embodiment 1, wherein at least one of the one or more second polymeric portions comprise a thermoplastic elastomer.

Embodiment 3 is the device of embodiment 1 or 2, wherein the one or more second polymeric portions comprises a material having a durometer less than or equal to 55D.

Embodiment 4 is the device of any of embodiments 1 through 3, wherein the one or more second polymeric portions are resilient such that the one or more second polymeric portions are compressible under application of force from an uncompressed state to a compressed state.

Embodiment 5 is the device of any of embodiments 1 through 4, wherein the one or more first polymeric portions defines an outer surface, and wherein the one or more second polymeric portions define a contact surface configured to contact at least one of the one or more components or the housing, wherein the contact surface is located away from the outer surface of the first polymeric portion, wherein the contact surface of the second polymeric portion is located closer to the outer surface of the one or more first polymeric portions when in the compressed state than when in the uncompressed state.

Embodiment 6 is the device of any of embodiments 1 through 5, wherein the housing applies a compressive force to the one or more second polymeric portions to provide the interference fit between the one or more second polymeric portions and at least one of the housing and the one or more components.

Embodiment 7 is the device of any of embodiments 1 through 6, wherein a height is defined between the contact surface and the outer surface, wherein when at least one of the one or more second polymeric portions is in the compressed state, the height is less than 90% of the height when the at least one of the one or more second polymeric portions is in the uncompressed state.

Embodiment 8 is the device of any of embodiments 1 through 7, wherein the one or more first polymeric portions defines a first surface, a second surface opposite the first surface, and one or more openings extending through the one or more first polymeric portions from the first surface to the second surface, wherein at least a portion of at least one of the one or more components is located within at least one of the one or more openings.

Embodiment 9 is the device of any of embodiments 1 through 8, wherein the one or more first polymeric portion defines a first surface, a second surface opposite the first surface, and one or more apertures extending from the first surface to the second surface, and wherein at least a portion of at least one of the one or more second polymeric portions is located within at least one of the one or more apertures.

Embodiment 10 is the device of any of embodiments 1 through 9, wherein the one or more first polymeric portions defines an outer perimeter, and wherein at least a portion of the one or more second polymeric portions is coupled to the first polymeric portion proximate the outer perimeter.

Embodiment 11 is the device of any of embodiments 1 through 9, wherein the one or more first polymeric portions defines an outer perimeter, and wherein at least one of the one or more second polymeric portions is not exposed to the outer perimeter.

Embodiment 12 is the device of any of embodiments 1 through 11, wherein at least one of the one or more first polymeric portions and/or at least one of the one or more second polymeric portions comprise a desiccant.

Embodiment 13 is the device of any of embodiments 1 through 12, wherein the one or more second polymeric portions comprise a polymer including a desiccant material, wherein the second polymeric portions are configured to absorb 0.1-300 milligrams of moisture per gram of the polymer including the desiccant material at 0.1-300 hours exposure to 0-70% relative humidity.

Embodiment 14 is the device of any of embodiments 1 through 12, wherein the one or more second polymeric portions comprise a polymer including a desiccant material, wherein the second polymeric portions are configured to absorb 50-120 milligrams of moisture per gram of the polymer including the desiccant material at 200 hours exposure to 20-50% relative humidity.

Embodiment 15 is the device of any of embodiments 12 through 14, wherein the desiccant is selected from calcium oxide, silica gel, activated alumina, clay, natural zeolites, anhydrous magnesium, calcium sulfate, starches, molecular sieves, aluminosilicates, polyanhydrides, and combinations thereof.

Embodiment 16 is the device of any of embodiments 1 through 15, wherein at least one of the one or more first polymeric portions and/or the one or more second polymeric portions comprise a sorbent.

Embodiment 17 is the device of embodiment 16, wherein the sorbent comprises activated carbon.

Embodiment 18 is the device of embodiment 16 or 17, wherein the sorbent comprises a hydrogen gas sorbent.

Embodiment 19 is the device of any of embodiments 1 through 18, wherein at least one of the one or more first polymeric portions or at least one of the one or more second polymeric portions comprises a radiopaque material.

Embodiment 20 is the device of any of embodiments 1 through 19, wherein the one or more second polymeric portions comprise an SEBS thermoplastic elastomer mixed with a molecular sieve powder desiccant.

Embodiment 21 is the device of any of embodiments 1 through 20, wherein the one or more second polymeric portions comprise an EPDM/PP thermoplastic elastomer blend mixed with a molecular sieve powder desiccant.

Embodiment 22 is the device of any of embodiments 1 through 20, wherein the one or more second polymeric portions comprise thermoplastic polyether-polyurethane copolymer elastomer mixed with a molecular sieve powder desiccant.

Embodiment 23 is the device of any of embodiments 1 through 20, wherein the one or more second polymeric portions comprise a crystalline polyethylene (PE) polymer mixed with a molecular sieve powder desiccant.

Embodiment 24 is the device of any of embodiments 1 through 23, wherein the one or more first polymeric portions have a durometer greater than or equal to 90D, and the one or more second polymeric portions have a durometer less than or equal to 90A on the Shore Durometer Scale.

Embodiment 25 is the device of any of embodiments 1 through 23, wherein the one or more first polymeric portions have a durometer greater than or equal to 100 on Rockwell R scale, and the one or more second polymeric portions have a durometer less than or equal to 80A on Shore Durometer scale.

Embodiment 26 is the device of any of embodiments 1 through 25, wherein the one or more first polymeric portions comprise a polymer selected from liquid crystalline polymers, polyetherether ketone, polysulfone, polypropylene, polystyrene, acrylonitrile butadiene styrene copolymer, polycarbonate, polyvinyl chloride, poly(methyl methacrylate), polyphenol oxide, polyimide, polyamide, polymethylene oxide, polyurethane, polyurea, polyester, acrylonitrile-butadiene-styrene copolymer (ABS), and blends or copolymers thereof.

Embodiment 27 is the device of any of embodiments 1 through 26, wherein the one or more first polymeric portions further comprise fibers.

Embodiment 28 is the device of any of embodiments 1 through 27, wherein the one or more second polymeric portions comprise an elastomeric polymer selected from low density polyethylene, ethylene-propylene copolymers, ethylene-butadiene copolymer, ethylene-propylene-diene monomer (EPDM), polybutadiene, polyvinylacetate, nitrile-butadiene copolymer, polyisoprene, silicone, fluoropolymer, polyether, polyester, polycarbonate, polyurethane, polyether-polyurethane copolymer, polyester, polyamide, and blends or copolymers thereof.

Embodiment 29 is the device of any of embodiments 1 through 28, wherein the one or more second polymer portions comprise copolymers of the elastomeric polymer with non-elastomeric polymers, plasticized polymers, elastomer-glass polymer blends, and elastomer-crystalline polymer blends.

Embodiment 30 is a method of manufacturing an implantable medical device, wherein the method comprises:
providing a housing defining an interior space;
providing one or more components;
providing one or more first polymeric portions;
coupling one or more second polymeric portions to the one or more first polymeric portions to form a frame, wherein at least one of the one or more first polymeric portions has a higher durometer than at least one of the one or more second polymeric portions;
inserting the one or more components and the frame into the interior space of the housing; and
closing the housing, providing an interference fit between the one or more second polymeric portions and at least one of the housing and the one or more components.

Embodiment 31 is the method of embodiment 30, wherein at least one of the one or more first polymeric portions and the one or more second polymeric portions comprise a desiccant material.

Embodiment 32 is the method of embodiments 30 or 31, wherein providing the one or more first polymeric portions comprises:
providing a first mold defining a first cavity for forming the one or more first polymeric portions;
introducing a first moldable material into the first cavity of the first mold to form the one or more first polymeric portions; and
forming the one or more first polymeric portions from the first moldable material within the first cavity of the mold.

Embodiment 33 is the method of embodiments 30 or 31, wherein providing the one or more first polymeric portions comprises:
providing a first mold defining a first cavity for forming the one or more first polymeric portions;
introducing a first moldable material into the first cavity of the first mold to form the one or more first polymeric portions; and
forming the one or more first polymeric portions from the first moldable material within the first cavity; and
wherein coupling the one or more second polymeric portions to the one or more first polymeric portions comprises:
providing a second mold defining a second cavity for forming a second polymeric portion;
positioning the one or more first polymeric portions into the second cavity; and
introducing a second moldable material into the second cavity of the second mold to form the one or more second polymeric portions and to couple the one or more second polymeric portions to the one or more first polymeric portions.

Embodiment 34 is the method of embodiment 33, wherein the second mold comprises at least a portion of the first mold.

Embodiment 35 is an implantable medical device comprising:
a housing defining an interior space;
one or more components disposed in the interior space of the housing;
a frame disposed in the interior space of the housing, wherein the frame comprises:
one or more first polymeric portions; and
one or more second polymeric portions coupled to the one or more first polymeric portions;
wherein at least one of the one or more first polymeric portions is made of the same material as at least one of the one or more second polymeric portions; and
wherein the one or more second polymeric portions provides an interference fit between the one or more second polymeric portions and at least one of the housing and the one or more components disposed in the interior space of the housing.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the exemplary apparatus described herein. Various modifications of the illustrative embodiments, as well as additional embodiments of the disclosure, will be apparent upon reference to this description.

What is claimed:

1. An implantable medical device comprising:
   a housing defining an interior space;
   one or more components disposed in the interior space of the housing;
   a frame disposed in the interior space of the housing, wherein the frame comprises:
   one or more first polymeric portions; and
   one or more second polymeric portions coupled to the one or more first polymeric portions;
   wherein at least one of the one or more first polymeric portions has a higher durometer than at least one of the one or more second polymeric portions; and
   wherein the one or more second polymeric portions provides an interference fit between the one or more second polymeric portions and at least one of the housing and the one or more components disposed in the interior space of the housing.

2. The device of claim 1, wherein at least one of the one or more second polymeric portions comprise a thermoplastic elastomer.

3. The device of claim 1, wherein the one or more second polymeric portions comprises a material having a durometer less than or equal to 55D.

4. The device of claim 1, wherein the one or more second polymeric portions are resilient such that the one or more second polymeric portions are compressible under application of force from an uncompressed state to a compressed state.

5. The device of claim 4, wherein the one or more first polymeric portions defines an outer surface, and wherein the one or more second polymeric portions define a contact surface configured to contact at least one of the one or more components or the housing, wherein the contact surface is located away from the outer surface of the first polymeric portion, wherein the contact surface of the second polymeric portion is located closer to the outer surface of the one or more first polymeric portions when in the compressed state than when in the uncompressed state.

6. The device of claim 5, wherein the housing applies a compressive force to the one or more second polymeric portions to provide the interference fit between the one or more second polymeric portions and at least one of the housing and the one or more components.

7. The device of claim 1, wherein the one or more first polymeric portions defines a first surface, a second surface opposite the first surface, and one or more openings extending through the one or more first polymeric portions from the first surface to the second surface, wherein at least a portion of at least one of the one or more components is located within at least one of the one or more openings.

8. The device of claim 1, wherein the one or more first polymeric portion defines a first surface, a second surface opposite the first surface, and one or more apertures extending from the first surface to the second surface, and wherein at least a portion of at least one of the one or more second polymeric portions is located within at least one of the one or more apertures.

9. The device of claim 1, wherein the one or more first polymeric portions defines an outer perimeter, and wherein at least a portion of the one or more second polymeric portions is coupled to the first polymeric portion proximate the outer perimeter.

10. The device of claim 1, wherein the one or more first polymeric portions defines an outer perimeter, and wherein at least one of the one or more second polymeric portions is not exposed to the outer perimeter.

11. The device of claim 1, wherein at least one of the one or more first polymeric portions and/or at least one of the one or more second polymeric portions further comprise a desiccant.

12. The device of claim 11, wherein the one or more second polymeric portions comprise a polymer including a desiccant material, wherein the second polymeric portions are configured to absorb 0.1-300 milligrams of moisture per gram of the polymer including the desiccant material at 0.1-300 hours exposure to 0-70% relative humidity.

13. The device of claim 12, wherein the one or more second polymeric portions comprise a polymer including a desiccant material, wherein the second polymeric portions are configured to absorb 50-120 milligrams of moisture per gram of the polymer including the desiccant material at 200 hours exposure to 20-50% relative humidity.

14. The device of claim 1, wherein at least one of the one or more first polymeric portions and/or the one or more second polymeric portions further comprise a sorbent.

15. The device of claim 14, wherein the sorbent comprises activated carbon.

16. The device of claim 14, wherein the sorbent comprises a hydrogen gas sorbent.

17. The device of claim 1, wherein the one or more second polymeric portions comprise an SEBS thermoplastic elastomer mixed with a molecular sieve powder desiccant.

18. The device of claim 1, wherein the one or more second polymeric portions comprise an EPDM/PP thermoplastic elastomer blend mixed with a molecular sieve powder desiccant.

19. The device of claim 1, wherein the one or more second polymeric portions comprise thermoplastic polyether-polyurethane copolymer elastomer mixed with a molecular sieve powder desiccant.

20. The device of claim 1, wherein the one or more second polymeric portions comprise a crystalline polyethylene (PE) polymer mixed with a molecular sieve powder desiccant.

21. The device of claim 1, wherein the one or more first polymeric portions have a durometer greater than or equal to 90D, and the one or more second polymeric portions have a durometer less than or equal to 90A on the Shore Durometer Scale.

22. The device of claim 1, wherein the one or more first polymeric portions have a durometer greater than or equal to 100 on Rockwell R scale, and the one or more second polymeric portions have a durometer less than or equal to 80A on Shore Durometer scale.

23. A method of manufacturing an implantable medical device, wherein the method comprises:
   providing a housing defining an interior space;
   providing one or more components;
   providing one or more first polymeric portions;
   coupling one or more second polymeric portions to the one or more first polymeric portions to form a frame, wherein at least one of the one or more first polymeric portions has a higher durometer than at least one of the one or more second polymeric portions;

inserting the one or more components and the frame into the interior space of the housing; and closing the housing, providing an interference fit between the one or more second polymeric portions and at least one of the housing and the one or more components.

24. The method of claim 23, wherein at least one of the one or more first polymeric portions and the one or more second polymeric portions further comprise a desiccant material.

25. The method of claim 23, wherein providing the one or more first polymeric portions comprises:

providing a first mold defining a first cavity for forming the one or more first polymeric portions;

introducing a first moldable material into the first cavity of the first mold to form the one or more first polymeric portions; and forming the one or more first polymeric portions from the first moldable material within the first cavity of the mold.

26. The method of claim 23, wherein providing the one or more first polymeric portions comprises:

providing a first mold defining a first cavity for forming the one or more first polymeric portions;

introducing a first moldable material into the first cavity of the first mold to form the one or more first polymeric portions; and forming the one or more first polymeric portions from the first moldable material within the first cavity; and wherein coupling the one or more second polymeric portions to the one or more first polymeric portions comprises:

providing a second mold defining a second cavity for forming a second polymeric portion;

positioning the one or more first polymeric portions into the second cavity; and introducing a second moldable material into the second cavity of the second mold to form the one or more second polymeric portions and to couple the one or more second polymeric portions to the one or more first polymeric portions.

27. The method of claim 26, wherein the second mold comprises at least a portion of the first mold.

* * * * *